US008963555B2

(12) United States Patent
Wu et al.

(10) Patent No.: US 8,963,555 B2
(45) Date of Patent: Feb. 24, 2015

(54) METHODS, SYSTEMS, AND APPARATUS FOR DETECTING LIGHT AND ACOUSTIC WAVES

(75) Inventors: Juntao Wu, Niskayuna, NY (US); Glenn Alan Forman, Niskayuna, NY (US); Michael Shane Pilon, Markham (CA); Zhihong Roy Mao, Stouffville (CA); Chun Zhan, Niskayuna, NY (US); Maxine Marie Gibeau, Slingerlands, NY (US); Lubomir Hristov Sevov, Mount Albert (CA)

(73) Assignee: General Electric Company, Schenectady, NY (US)

( * ) Notice: Subject to any disclaimer, the term of this patent is extended or adjusted under 35 U.S.C. 154(b) by 908 days.

(21) Appl. No.: 13/107,044

(22) Filed: May 13, 2011

(65) Prior Publication Data
US 2012/0286795 A1 Nov. 15, 2012

(51) Int. Cl.
*G01R 31/00* (2006.01)
(52) U.S. Cl.
USPC .............................. 324/501; 324/500; 324/536
(58) Field of Classification Search
CPC ..... G01H 9/004; G01H 9/00; G01N 29/2418; G01R 31/311; G01R 31/305; G01R 31/309; G01R 31/002; G01R 31/026
USPC ........................................................ 324/501
See application file for complete search history.

(56) References Cited

U.S. PATENT DOCUMENTS

| 6,141,192 | A | 10/2000 | Garzon |
| 6,693,438 | B2 | 2/2004 | Shea |
| 7,142,291 | B2 | 11/2006 | Sarkozi et al. |
| 7,391,508 | B2 * | 6/2008 | Grodzins ........................ 356/72 |
| 7,473,906 | B2 | 1/2009 | Egalon |
| 7,536,914 | B2 | 5/2009 | Land, III et al. |
| 7,668,412 | B2 | 2/2010 | Lee et al. |
| 7,806,000 | B2 | 10/2010 | Land, III et al. |
| 2002/0130668 | A1 * | 9/2002 | Blades ........................ 324/536 |
| 2010/0072352 | A1 | 3/2010 | Kesler et al. |
| 2010/0328824 | A1 | 12/2010 | Roscoe |
| 2012/0092965 | A1 * | 4/2012 | Zhou et al. .................... 367/135 |

OTHER PUBLICATIONS

Ultrasonic Sensors, Wikipedia, including condenser microphones, updated 2014, p. 1-6.*
Katsutoshi Muto, Electric-Discharge Sensor Utilizing Fluorescent Optical Fiber, Jul. 1989, vol. 7, Issue 7, pp. 1029-1032, Journal of Light Wave Technology.

* cited by examiner

*Primary Examiner* — Thomas F Valone
(74) *Attorney, Agent, or Firm* — General Electric Company (57) ABSTRACT

A sensor includes a sensor head including an acoustic detector configured to receive light from a first light source and to reflect the light upon incidence of acoustic waves. The sensor also includes at least one optical fiber and at least one fluorescent material within at least one of the sensor head and the at least one optical fiber. The at least one fluorescent material is configured to receive light from a second light source external to the sensor and emit visible light in response to the light received from the second light source.

20 Claims, 4 Drawing Sheets

METHODS, SYSTEMS, AND APPARATUS FOR DETECTING LIGHT AND ACOUSTIC WAVES

BACKGROUND OF THE INVENTION

The embodiments described herein relate generally to detection systems and, more particularly, to methods, systems, and apparatus for detecting light and acoustic waves.

Known electric power circuits and switchgear generally have conductors that are separated by insulation, such as air, or gas or solid dielectrics. However, if the conductors are positioned too closely together, or if a voltage between the conductors exceeds the insulative properties of the insulation between the conductors, an arc can occur. The insulation between the conductors can become ionized, which makes the insulation conductive and enables arc formation.

An arc flash is caused by a rapid release of energy due to a fault between two phase conductors, between a phase conductor and a neutral conductor, or between a phase conductor and a ground point. Arc flash temperatures can reach or exceed 20,000° C., which can vaporize the conductors and adjacent equipment. In addition, an arc flash can release significant energy in the form of heat, intense light, pressure waves, and/or sound waves, sufficient to damage the conductors and adjacent equipment. However, the current level of a fault that generates an arc flash is generally less than the current level of a short circuit, such that a circuit breaker generally does not trip or exhibits a delayed trip unless the circuit breaker is specifically designed to handle an arc fault condition. Although agencies and standards exist to regulate arc flash issues by mandating the use of personal protective clothing and equipment, there is no device established by regulation that eliminates arc flash.

Standard circuit protection devices, such as fuses and circuit breakers, generally do not react quickly enough to mitigate an arc flash. One known circuit protection device that exhibits a sufficiently rapid response is an electrical "crowbar," which utilizes a mechanical and/or electro-mechanical process by intentionally creating an electrical "short circuit" to divert the electrical energy away from the arc flash point. Such an intentional short circuit fault is then cleared by tripping a fuse or a circuit breaker. However, the intentional short circuit fault created using a crowbar may allow significant levels of current to flow through adjacent electrical equipment, thereby still enabling damage to the equipment.

Light sensors may be used to detect the presence of light emitted during an arc flash. However, such sensors are often sensitive to low light levels such that they also detect non-arc-flash light and trigger a "nuisance trip" of a circuit protection device. For example, a typical arc flash event can produce light with luminous flux on the order of 100,000 lux at a distance of three to four feet from the arc flash event, while known light sensors generally saturate at 700 lux or less. Light emitted by a circuit breaker during a trip, by space lighting, or by direct sunlight may cause the light sensor to falsely detect an arc flash event. At least some known arc flash detection systems using a particular venting pattern or light sensors that are positioned such that light released during a circuit breaker interruption, for example, does not sufficiently saturate the light sensor. However, reducing the amount of light released during a circuit breaker interruption can negatively affect circuit breaker performance. Thus, there is a need for an arc flash detection system that reliably detects arc flash events and mitigates undesired nuisance trips of circuit protection devices.

BRIEF DESCRIPTION OF THE INVENTION

In one embodiment, a sensor is provided that includes a sensor head including an acoustic detector configured to receive light from a first light source and to reflect the light upon incidence of acoustic waves. The sensor also includes at least one optical fiber and at least one fluorescent material within at least one of the sensor head and the at least one optical fiber. The at least one fluorescent material is configured to receive light from a second light source external to the sensor and emit visible light in response to the light received from the second light source.

In another embodiment, a detection system is provided that includes a sensor. The sensor includes a sensor head including an acoustic detector configured to receive light from a first light source and reflect the light upon incidence of acoustic waves. The sensor also includes at least one optical fiber and at least one fluorescent material within at least one of the sensor head and the at least one optical fiber. The at least one fluorescent material is configured to receive light from a second light source external to the sensor and emit visible light in response to the light received from the second light source. The detection system also includes a signal processing device including a processor programmed to receive a first measurement representative of the light reflected by the acoustic detector, receive a second measurement representative of the visible light emitted from the at least one fluorescent material, and determine the occurrence of an arc flash based on the reflected light and the visible light received.

In yet another embodiment, a method of detecting an arc flash using at least one sensor is provided that includes receiving at least one acoustic wave by an acoustic detector positioned within the at least one sensor and reflecting light, by the acoustic detector, due to vibrations caused by the at least one acoustic wave. The method also includes receiving light from a source external to the at least one sensor, transforming the light received from the external source into visible light, and detecting the occurrence of an arc flash based on the reflected light and the visible light.

DETAILED DESCRIPTION OF THE INVENTION

Figure 1:
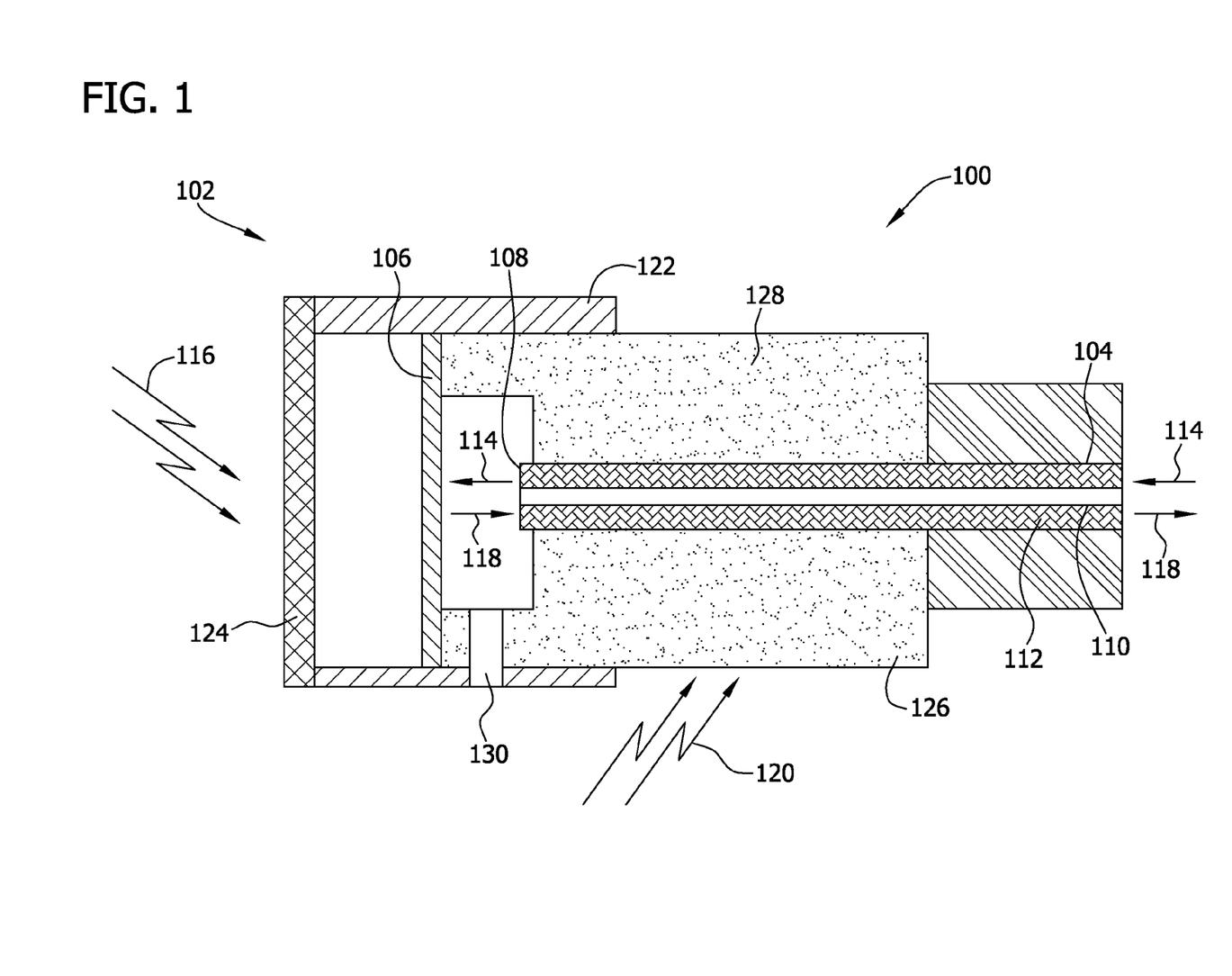
FIG. 1 is a cross-sectional view of an exemplary sensor for use in detecting an arc flash.

FIG. 1 is a cross-sectional view of an exemplary sensor 100 that may be used to detect an arc flash. In an exemplary embodiment, sensor 100 includes a sensor head 102 and at least one optical fiber 104. Sensor head 102 includes an acoustic detector 106, such as a diaphragm 106, positioned proximate a downstream end 108 of optical fiber 104 having a fiber core 110 and a fiber sheath 112. A light beam 114 is transmitted downstream through optical fiber 104, i.e., through fiber core 110, and is directed onto diaphragm 106. Acoustic waves 116 and/or pressure waves generated, for example, by an arc flash, cause diaphragm 106 to vibrate and cause a reflection 118 of light beam 114 (hereinafter referred to as "reflected light 118") upstream through fiber core 110. The vibration of diaphragm 106 causes one or more characteristics of reflected light 118, such as an intensity, a phase, a polarization, and/or a frequency of light 118, to be different from the characteristics of light beam 114.

As used herein, the term "downstream" refers to a direction toward downstream end 108 of optical fiber 104 and substantially parallel to fiber 104. As used herein, the term "upstream" refers to a direction away from downstream end 108 of optical fiber 104 and substantially parallel to fiber 104. In addition, as used herein, an "arc flash" refers to a rapid release of energy due to a fault between two electrical conductors. The rapid release of energy causes acoustic waves 116 and light 120 to be generated proximate the fault, for example, in an environment external to sensor 100.

In an alternative embodiment, sensor 100 includes two or more optical fibers 104. In such an embodiment, one optical fiber 104 transmits light beam 114 to diaphragm 106, and another optical fiber 104 transmits reflected light 118 upstream for processing and/or analysis, as described more fully herein.

In an exemplary embodiment, diaphragm 106 includes an opaque material made of thin film and disposed in an elongated position. Diaphragm 106 vibrates upon incidence of acoustic waves 116 and/or upon incidence of other suitable pressure waves. To protect diaphragm 106 during operation, diaphragm 106 is enclosed within a protective sleeve 122 and a protective screen 124 that enables acoustic waves 116 to reach diaphragm 106.

A fiber holder 126 is positioned about, and coupled to, optical fiber 104. Fiber holder 126 includes a semi-transparent region 128 configured to diffuse light originating from the arc flash into fiber core 110. In an exemplary embodiment, semi-transparent region 128 is coated with a fluorescent material and/or a fluorescent material is within region 128. Accordingly, in an exemplary embodiment, the fluorescent material of semi-transparent region 128 enables light 120, such as ultraviolet light 120, entering region 128 to be transformed into visible light of a different spectrum or wavelength than entering light 120. More specifically, the fluorescent material absorbs ultraviolet light 120 entering semi-transparent region 128 and emits light in one or more visible wavelengths (hereinafter "visible light") towards or into fiber core 110.

In one embodiment, one or more openings 130 are defined within semi-transparent region 128 to enhance the light detection from an arc flash. In one embodiment, openings 130 are about 0.5 millimeters (mm) to about 2 mm in diameter. Alternatively, openings 130 may have any suitable diameter that enables sensor 100 to function as described herein. Light 120 generated by an arc flash is directed through openings 130 towards fiber core 110. In another embodiment, protective screen 124 and diaphragm 106 enable an amount of light to be directed to fiber core 110.

During operation, fiber core 110 directs light beam 114 onto diaphragm 106. If an arc flash occurs, diaphragm 106 vibrates based on the intensity and frequency of acoustic waves 116 generated from the arc flash. Based on the vibrations, a unique pattern of light is reflected from diaphragm 106. A distance between downstream end 108 of optical fiber 104 and diaphragm 106 is optimized such that the light reflected from diaphragm 106 is received by fiber core 110 without significant transmission losses. In addition, light 120 generated by the arc flash is absorbed by semi-transparent region 128, and is transformed into visible light by the fluorescent material of region 128. Semi-transparent region 128 emits the visible light towards fiber core 110. The light reflected by diaphragm 106 and the visible light emitted from the fluorescent material of semi-transparent region 128 is processed and/or analyzed to detect the occurrence of an arc flash, as described more fully herein. Such an integrated approach of sensing acoustic waves 116 and light 120 minimizes false alarms and enables early arc flash detection.

Figure 2:
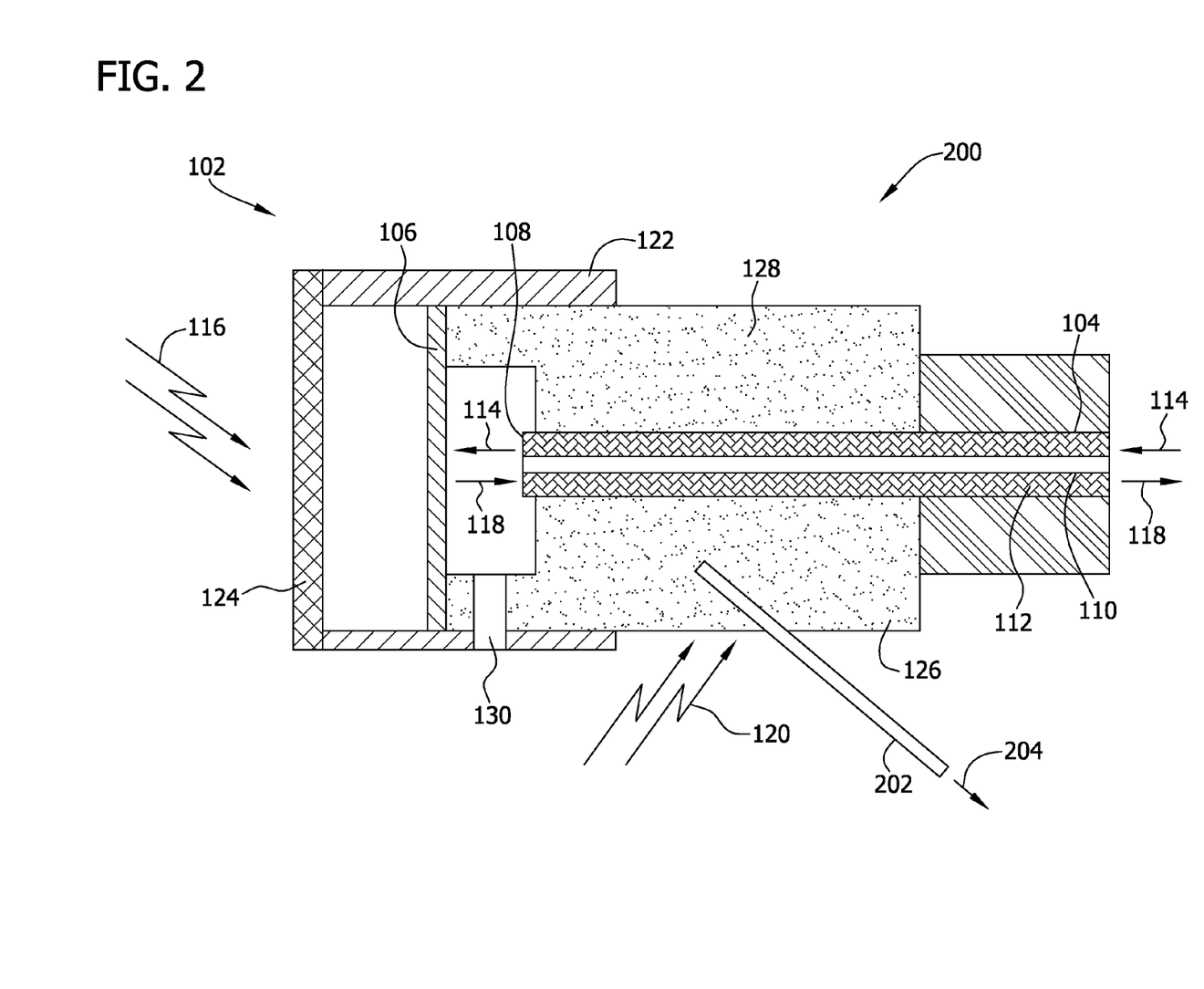
FIG. 2 is a cross-sectional view of another exemplary sensor for use in detecting an arc flash.

FIG. 2 is a cross-sectional view of an exemplary sensor 200 that may be used to detect an arc flash. Unless otherwise specified, sensor 200 is similar to sensor 100 (shown in FIG. 1), and similar components are labeled in FIG. 2 with the same reference numerals used in FIG. 1. In an exemplary embodiment, sensor 200 includes a first optical fiber 104 and a second optical fiber 202. First optical fiber 104 transmits light beam 114 to diaphragm 106 and transmits light 118 reflected by diaphragm 106 for use in detecting acoustic waves 116 generated by an arc flash. Second optical fiber 202 is coupled to fiber holder 126 upstream from diaphragm 106. In addition, second optical fiber 202 is coated with a fluorescent material and/or a fluorescent material is within fiber 202. Accordingly, second optical fiber 202 absorbs light 120, such as ultraviolet light 120 generated by an arc flash, and emits visible light 204. Visible light 204 and light 118 reflected by diaphragm 106 are processed and/or analyzed to determine whether an arc flash occurred, as described more fully herein. Alternatively, sensor 200 does not include second optical fiber 202, and first optical fiber 104 includes a fluorescent material as described above.

In an exemplary embodiment, semi-transparent region 128 does not include a fluorescent material such that second optical fiber 202, rather than region 128, emits visible light 204 in response to light generated by an arc flash. Alternatively, both second optical fiber 202 and semi-transparent region 128 include one or more fluorescent materials such that fiber 202 and region 128 emit visible light 204 in response to light 120 generated by an arc flash. Visible light 204 emitted from second optical fiber 202 and semi-transparent region 128 is processed and/or analyzed, as described more fully herein.

Figure 3:
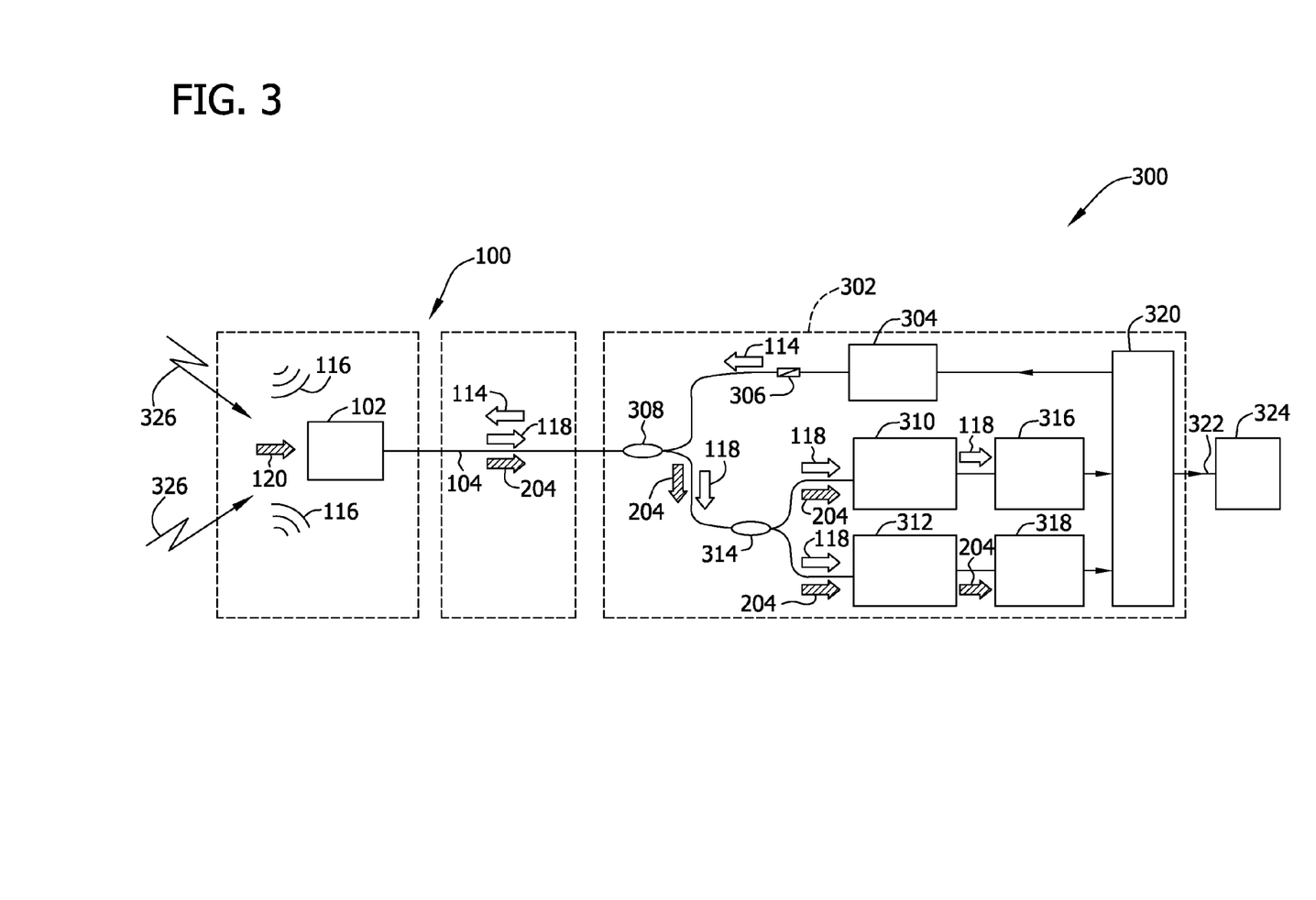
FIG. 3 is a block diagram of an exemplary detection system for use in detecting an arc flash.

FIG. 3 is a block diagram of an exemplary detection system 300 that may be used to detect an arc flash within a switchgear and/or any other electrical circuit or power system (none shown). In an exemplary embodiment, detection system 300 includes a signal processing device 302 and sensor 100 including optical fiber 104 coupled to sensor head 102. While detection system 300 is described with reference to sensor 100, it should be recognized that detection system 300 may include sensor 200 instead of, or in addition to, sensor 100.

Signal processing device 302 includes a light source 304 coupled to optical fiber 104 by an isolator 306 and a fiber splitter 308. In one embodiment, light source 304 includes a light-emitting diode. In another embodiment, light source 304 includes a laser diode that emits light at about near infrared wavelengths. In an exemplary embodiment, isolator 306 prevents reflected light 118 and/or visible light 204 from entering light source 304.

In an exemplary embodiment, signal processing device 302 includes a fiber splitter 308 that directs light beam 114 downstream from light source 304 to sensor head 102, and directs reflected light 118 and visible light 204 upstream to a first optical filter 310 and a second optical filter 312 within signal processing device 302. In one embodiment, a fiber coupler 314 is coupled to fiber splitter 308. In such an embodiment, fiber coupler 314 directs reflected light 118 and visible light 204 to first optical filter 310 and to second optical filter 312.

First and second optical filters 310 and 312 enable predetermined wavelengths of light to be transmitted to a first photo detector 316 and to a second photo detector 318, and filter out or block remaining wavelengths of light. In one embodiment, first and second optical filters 310 and 312 each include a band-pass filter. Alternatively, first optical filter 310 and/or second optical filter 312 may include any other filter that enables signal processing device 302 to function as described herein. In an exemplary embodiment, first optical filter 310 filters out wavelengths that are above and below an expected range of wavelengths of reflected light 118. Accordingly, visible light 204 is filtered out by first optical filter 310 and reflected light 118 is output from filter 310. Second optical filter 312 filters out wavelengths that are above and below an expected range of wavelengths of visible light 204. Accordingly, reflected light 118 is filtered out by second optical filter 312 and visible light 204 is output from filter 312.

First photo detector 316 receives reflected light 118 from first optical filter 310 and second photo detector 318 receives visible light 204 from second optical filter 312. First and second photo detectors 316 and 318 generate a proportional or a representative voltage signal based upon the intensity and wavelength of incident light.

In an exemplary embodiment, signal processing device 302 includes a processor 320 that receives the voltage signals from first photo detector 316 and second photo detector 318. Processor 320 analyzes the voltage signals, as described more fully herein, and generates an arc fault signal 322 if processor 320 determines that an arc flash has occurred.

Processor 320 includes any suitable programmable circuit which may include one or more systems and microcontrollers, microprocessors, reduced instruction set circuits (RISC), application specific integrated circuits (ASIC), programmable logic circuits (PLC), field programmable gate arrays (FPGA), and any other circuit capable of executing the functions described herein. The above examples are exemplary only, and thus are not intended to limit in any way the definition and/or meaning of the term "processor."

In an exemplary embodiment, processor 320 is coupled to, or includes, a memory device (not shown). The memory device includes a computer readable medium, such as, without limitation, random access memory (RAM), flash memory, a hard disk drive, a solid state drive, a diskette, a flash drive, a compact disc, a digital video disc, and/or any suitable memory that enables processor 320 to store, retrieve, and/or execute instructions and/or data. Processor 320 receives instructions from the memory device that program processor 320 to perform the steps and functions described herein.

A protective device 324 is coupled to processor 320 to mitigate the detected arc flash. In one embodiment, protective device 324 includes a relay configured to "trip", or activate, upon receiving a signal, such as arc fault signal 322. Upon activation of protective device 324, current is prevented from flowing through conductors (not shown) proximate the detected arc fault.

During operation, acoustic waves 116 and light 120 are emitted from an arc flash 326 and are detected by sensor 100. More specifically, light 120 is absorbed by the fluorescent material of semi-transparent region 128, first optical fiber 104, and/or second optical fiber 202, and visible light 204 emitted from region 128, fiber 104, and/or fiber 202 is transmitted to signal processing device 302. In addition, light source 304 transmits light beam 114 to diaphragm 106 (shown in FIG. 1). Acoustic waves 116 cause diaphragm 106 to vibrate and cause light beam 114 to be reflected by diaphragm 106 as reflected light 118. In an exemplary embodiment, reflected light 118 is transmitted to signal processing device 302.

Reflected light 118 and/or visible light 204 is transmitted to signal processing device 302 through at least one optical fiber 104. In an exemplary embodiment, reflected light 118 is transmitted to signal processing device 302 through first optical fiber 104, and visible light 204 is transmitted to signal processing device 302 through second optical fiber 202. Alternatively, reflected light 118 and/or visible light 204 may be transmitted to signal processing device 302 through any suitable number of optical fibers 104.

As reflected light 118 and visible light 204 are received by signal processing device 302, fiber coupler 314 directs reflected light 118 to first optical filter 310 and directs visible light 204 to second optical filter 312. Filtered reflected light 118 is output from first optical filter 310 and detected and/or measured by first photo detector 316. A first voltage signal representative of the measured or detected reflected light 118 (hereinafter referred to as the "reflected light measurement") is transmitted from first photo detector 316 to processor 320. In addition, filtered visible light 204 is output from second optical filter 312 and detected and/or measured by second photo detector 318. A second voltage signal representative of the measured or detected visible light 204 (hereinafter referred to as the "visible light measurement") is transmitted from second photo detector 318 to processor 320.

Processor 320 analyzes the signals from first and second photo detectors 316 and 318 and generates an arc fault signal 322 upon a detection of arc flash 326. More specifically, processor 320 compares the reflected light measurement to a predetermined first, or reflected light, threshold to determine whether the detected acoustic waves 116 are generated by an arc flash. Processor 320 compares the visible light measurement to a predetermined second, or visible light, threshold to determine whether the detected light 120 is generated by an arc flash. In addition, processor 320 determines a difference between the time that the visible light measurement is received and the time that the reflected light measurement is received (hereinafter referred to as a "timing gap"). Processor 320 compares the timing gap between the visible light measurement and the reflected light measurement to a predetermined timing range, or window to determine whether the received signals are generated by an arc flash. In an exemplary embodiment, the timing window is a predetermined time period in which the reflected light measurement is expected to be received (e.g., based on historical data, experimental data, or other suitable data) after the visible light measurement is received to indicate the occurrence of an arc flash. In one embodiment, the timing window is between about 500 microseconds and about 2 milliseconds. Alternatively, the timing window may be any suitable time period that enables detection system 300 to function as described herein.

In an exemplary embodiment, if the reflected light measurement equals or exceeds the reflected light threshold, the visible light measurement equals or exceeds the visible light threshold, and/or the timing gap is within the timing window, processor 320 generates arc fault signal 322 to indicate that an arc flash has occurred. Protective device 324 is activated based upon arc fault signal 322 and is configured to interrupt power to mitigate the arc flash. In one embodiment, arc fault signal 322 may be transmitted to a remote system (not shown) to generate an alarm, for error reporting, for storing data associated with arc flash 326, for display to a user, and/or for any desired purpose.

In an alternative embodiment, fiber coupler 314 and/or fiber splitter 308 may be omitted. In such an embodiment, light beam 114, reflected light 118, and/or visible light 204 may be transmitted through separate optical fibers 104. In another embodiment, fiber coupler 314 and/or fiber splitter 308 may be replaced by a single fiber coupler 314 that transmits light beam 114 to diaphragm 106, and that transmits reflected light 118 and visible light 204 to first optical filter 310 and to second optical filter 312.

Figure 4:
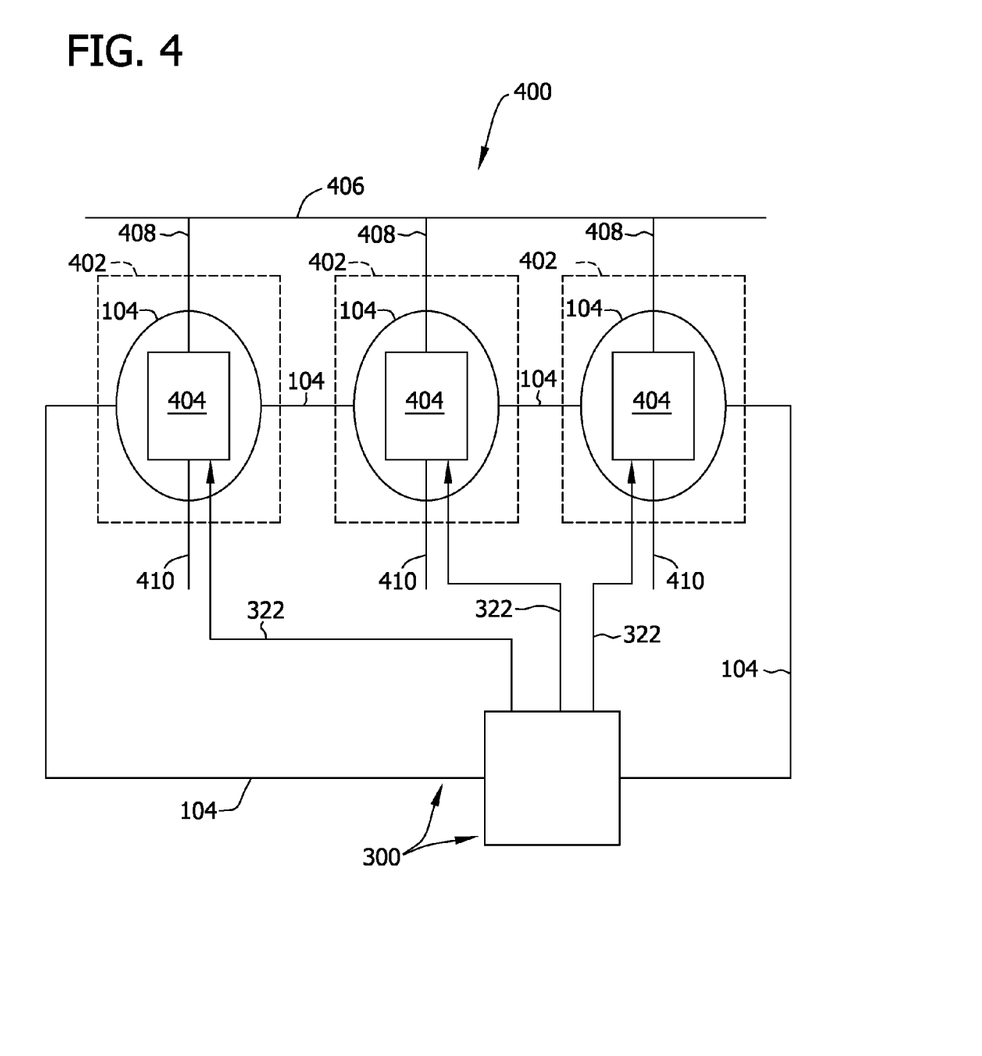
FIG. 4 is a block diagram of an exemplary power system.

FIG. 4 is a block diagram of an exemplary power system 400. In an exemplary embodiment, power system 400 includes detection system 300, a plurality of detection zones 402, and at least one circuit protection device 404 positioned within each detection zone 402.

In an exemplary embodiment, circuit protection devices 404 are coupled together by at least one conductor 406 or bus. Alternatively, one or more circuit protection devices 404 may be coupled to a separate conductor 406 or bus from other circuit protection devices 404. In an exemplary embodiment, circuit protection devices 404 include at least one circuit breaker that electrically connects or disconnects an input end 408 from an output end 410 of conductor 406 upon receipt of control signals, such as arc fault signal 322 from processor 320. Alternatively, circuit protection devices 404 include a relay or any other protection device that enables power system 400 to function as described herein.

In an exemplary embodiment, detection system 300 includes at least one optical fiber 104 positioned within at least one detection zone 402 and proximate at least one circuit protection device 404. In addition, optical fiber 104 includes at least one fluorescent material, as described more fully herein with respect to FIGS. 1-3. In an exemplary embodiment, optical fiber 104 is positioned within each detection zone 402 such that optical fiber 104 detects one or more arc flashes generated within detection zones 402.

In an exemplary embodiment, optical fiber 104 includes a different color of fluorescent material within each detection zone 402 such that optical fiber 104 emits a different color of visible light 204 within each detection zone 402 after absorbing light generated by an arc flash. As used herein, the term "color" refers to a predetermined range of wavelengths or spectra of visible light. Alternatively, detection system 300 may include a separate optical fiber 104 for each detection zone 402, and each optical fiber 104 includes a different color of fluorescent material.

If an arc flash occurs within a detection zone 402, optical fiber 104 associated with detection zone 402 absorbs light from the arc flash. The fluorescent material of optical fiber 104 within detection zone 402 emits visible light 204 (shown in FIG. 2) in the color associated with the fluorescent material and transmits visible light 204 to signal processing device 302 (shown in FIG. 3). Signal processing device 302 determines or detects the occurrence of an arc flash from visible light 204 as described above with reference to FIG. 3. In addition, signal processing device 302 analyzes the color (i.e., the wavelength and/or frequency) of visible light 204 received. More specifically, in an exemplary embodiment, signal processing device 302 includes a separate optical filter 310 and a separate photo detector 316 for each detection zone 402. Each optical filter 310 is tuned to the color of the fluorescent material used for each detection zone 402 such that filter 310 only allows the color of visible light 204 associated with the fluorescent material to pass through to photo detector 316. Photo detector 316 associated with each detection zone 402 transmits a visible light measurement (including data indicative of the color of light received) to processor 320.

In an exemplary embodiment, processor 320 references data stored in a look-up table or another data structure within a memory device (not shown) to correlate the color of light received from the arc flash with a detection zone 402 to determine the location (i.e., detection zone 402) in which the arc flash occurred. Processor 320 selects a predetermined visible light threshold associated with the determined location (i.e., the determined detection zone 402) where the arc flash occurred. In an exemplary embodiment, the visible light threshold for each detection zone 402 is different from the visible light threshold of each other detection zone 402. Processor 320 compares the visible light measurement received from photo detector 316 to the visible light threshold associated with detection zone 402 to determine if the light received is indicative of an arc flash, in a similar manner as described above. Detection system 300 transmits arc fault signal 322 to circuit protection device 404 or devices 404 within detection zone 402 associated with the detected arc flash to mitigate the arc flash. Accordingly, a plurality of detection zones 402 and circuit protection devices 404 may be efficiently monitored by detection system 300 to determine an occurrence, a time, and a location of an arc flash.

A technical effect of the systems and methods described herein includes at least one of (a) receiving at least one acoustic wave by a diaphragm positioned within at least one sensor; (b) reflecting light, by a diaphragm, due to vibrations caused by at least one acoustic wave; (c) receiving light from a source external to at least one sensor; (d) transforming light received from an external source into visible light; and (e) detecting the occurrence of an arc flash based on the reflected light and the visible light.

Exemplary embodiments of methods, systems, and apparatus for use in detecting light and acoustic waves are described above in detail. The methods, systems, and apparatus are not limited to the specific embodiments described herein but, rather, operations of the methods and/or components of the system and/or apparatus may be utilized independently and separately from other operations and/or components described herein. Further, the described operations and/or components may also be defined in, or used in combination with, other systems, methods, and/or apparatus, and are not limited to practice with only the systems, methods, and apparatus as described herein.

Although the present invention is described in connection with an exemplary electrical power system environment, embodiments of the invention are operational with numerous other general purpose or special purpose system environments or configurations. The system environment described herein is not intended to suggest any limitation as to the scope of use or functionality of any aspect of the invention. In addition, the system environment described herein should not be interpreted as having any dependency or requirement relating to any one or combination of components illustrated in the exemplary operating environment.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A sensor comprising:
  a sensor head comprising an acoustic detector configured to:
    receive a first light from a first light source; and
    reflect the first light in response to vibration caused by acoustic waves received at said acoustic detector;
  at least one optical fiber; and
  at least one fluorescent material within at least one of said sensor head and said at least one optical fiber, said at least one fluorescent material configured to:
    receive a second light from a second light source external to said sensor; and emit visible light in response to the second light received from the second light source.

2. A sensor in accordance with claim 1, wherein said sensor head comprises a semi-transparent region proximate said acoustic detector.

3. A sensor in accordance with claim 2, wherein said at least one fluorescent material is within said semi-transparent region.

4. A sensor in accordance with claim 1, wherein said at least one optical fiber comprises a first optical fiber for transmitting the first light from the first light source and the reflected first light, and a second optical fiber for transmitting the visible light emitted from said at least one fluorescent material.

5. A sensor in accordance with claim 1, wherein said acoustic detector is a diaphragm that vibrates upon reception of acoustic waves, wherein the vibration causes the first light from the first light source to be reflected by said diaphragm.

6. A detection system comprising:
a sensor comprising:
a sensor head comprising an acoustic detector configured to:
receive a first light from a first light source; and
reflect the first light in response to vibration caused by acoustic waves received at said acoustic detector;
at least one optical fiber; and
at least one fluorescent material within at least one of said sensor head and said at least one optical fiber, said at least one fluorescent material configured to:
receive a second light from a second light source external to said sensor; and
emit visible light in response to the second light received from the second light source; and
a signal processing device comprising a processor programmed to:
receive a first measurement representative of the reflected first light;
receive a second measurement representative of the visible light emitted from said at least one fluorescent material; and
determine the occurrence of an arc flash based on the reflected first light and the visible light received.

7. A detection system in accordance with claim 6, wherein said processor is further programmed to compare the first measurement to a reflected light threshold and to compare the second measurement to a visible light threshold.

8. A detection system in accordance with claim 7, wherein said processor is further programmed to calculate a timing gap representative of a difference between a time that said processor receives the first measurement and a time that said processor receives the second measurement.

9. A detection system in accordance with claim 8, wherein said processor is programmed to determine the occurrence of an arc flash upon a determination of at least one of
the first measurement equals or exceeds the reflected light threshold;
the second measurement equals or exceeds the visible light threshold; and
the timing gap is within a predetermined timing window.

10. A detection system in accordance with claim 9, wherein said processor is further programmed to activate a protection device to mitigate the arc flash upon the determination that the arc flash has occurred.

11. A detection system in accordance with claim 6, wherein said sensor head comprises a semi-transparent region proximate said acoustic detector, said at least one fluorescent material is within said semi-transparent region.

12. A detection system in accordance with claim 6, wherein said at least one optical fiber comprises a first optical fiber for transmitting the first light from the first light source and the reflected first light, and a second optical fiber for transmitting the visible light emitted from said at least one fluorescent material.

13. A method of detecting an arc flash using at least one sensor, said method comprising:
receiving at least one acoustic wave by an acoustic detector positioned within the at least one sensor;
reflecting a first light, by the acoustic detector, in response to vibrations caused by receiving the at least one acoustic wave at the acoustic detector;
receiving a second light from a source external to the at least one sensor;
transforming the second light received from the external source into visible light; and
detecting the occurrence of an arc flash based on the reflected first light and the visible light.

14. A method in accordance with claim 13, wherein said transforming the second light comprises absorbing the second light by a fluorescent material within the at least one sensor and emitting visible light from the fluorescent material.

15. A method in accordance with claim 13, further comprising:
generating a first measurement representative of the reflected first light;
generating a second measurement representative of the visible light;
comparing the first measurement to a reflected light threshold; and
comparing the second measurement to a visible light threshold.

16. A method in accordance with claim 15, further comprising calculating a timing gap representative of a difference between a time that the first measurement is received and a time that the second measurement is received.

17. A method in accordance with claim 16, wherein said detecting the occurrence of an arc flash comprises detecting the occurrence of an arc flash upon a determination of at least one of:
the first measurement equals or exceeds the reflected light threshold;
the second measurement equals or exceeds the visible light threshold; and
the timing gap is within a predetermined timing window.

18. A method in accordance with claim 13, wherein the at least one sensor includes a plurality of sensors, at least one sensor of the plurality of sensors positioned within each of a plurality of detection zones, said transforming the second light received from the external source into visible light comprises transforming the second light received by a first sensor of the plurality of sensors into visible light having a color that is different than a color of visible light emitted by each other sensor of the plurality of sensors.

19. A method in accordance with claim 18, further comprising:
receiving visible light from at least one sensor of the plurality of sensors; and
determining a location of the arc flash based on the color of visible light received.

20. A method in accordance with claim 19, further comprising determining a reflected light threshold and a visible light threshold for the at least one sensor of the plurality of sensors positioned in each detection zone.

* * * * *

UNITED STATES PATENT AND TRADEMARK OFFICE
CERTIFICATE OF CORRECTION

| | | |
|---|---|---|
| PATENT NO. | : 8,963,555 B2 | Page 1 of 1 |
| APPLICATION NO. | : 13/107044 | |
| DATED | : February 24, 2015 | |
| INVENTOR(S) | : Wu et al. | |

It is certified that error appears in the above-identified patent and that said Letters Patent is hereby corrected as shown below:

In the claims

In Column 9, Line 54, in Claim 9, delete "one of" and insert -- one of: --, therefor.

Signed and Sealed this
Twenty-seventh Day of October, 2015

Michelle K. Lee
*Director of the United States Patent and Trademark Office*